US012797311B2

(12) United States Patent
Takagi et al.

(10) Patent No.: US 12,797,311 B2
(45) Date of Patent: Nov. 17, 2026

(54) EMULSION COMPOSITION

(71) Applicant: KAO CORPORATION, Tokyo (JP)

(72) Inventors: Shunsuke Takagi, Odawara (JP); Hidetoshi Taima, Odawara (JP)

(73) Assignee: KAO CORPORATION, Tokyo (JP)

( * ) Notice: Subject to any disclaimer, the term of this patent is extended or adjusted under 35 U.S.C. 154(b) by 203 days.

(21) Appl. No.: 18/713,530

(22) PCT Filed: Nov. 22, 2022

(86) PCT No.: PCT/JP2022/043247
§ 371 (c)(1),
(2) Date: May 24, 2024

(87) PCT Pub. No.: WO2023/095810
PCT Pub. Date: Jun. 1, 2023

(65) Prior Publication Data

US 2025/0064693 A1 Feb. 27, 2025

(30) Foreign Application Priority Data

Nov. 26, 2021 (JP) ................................. 2021-192526

(51) Int. Cl.

*A61K 8/06* (2006.01)
*A61K 8/34* (2006.01)
*A61K 8/42* (2006.01)
*A61K 8/68* (2006.01)
*A61K 8/894* (2006.01)
*A61K 8/92* (2006.01)
*A61Q 19/00* (2006.01)

(52) U.S. Cl.
CPC .............. *A61K 8/064* (2013.01); *A61K 8/342* (2013.01); *A61K 8/42* (2013.01); *A61K 8/68* (2013.01); *A61K 8/894* (2013.01); *A61K 8/92* (2013.01); *A61Q 19/007* (2013.01)

(58) Field of Classification Search
None
See application file for complete search history.

(56) References Cited

U.S. PATENT DOCUMENTS

| | | | | |
|---|---|---|---|---|
| 9,295,621 B2 | | 3/2016 | Maes et al. | |
| 2014/0194522 A1 | * | 7/2014 | Kaizu .................. | A61Q 19/007 514/625 |
| 2020/0129390 A1 | | 4/2020 | Taima | |

FOREIGN PATENT DOCUMENTS

| | | | | | |
|---|---|---|---|---|---|
| EP | 2263639 A2 | * | 12/2010 | ............... A61K 8/06 |
| EP | 2742930 A1 | * | 6/2014 | ............. A61K 8/064 |
| FR | 3 094 891 A1 | | 10/2020 | |
| JP | 2005-179320 A | | 7/2005 | |
| JP | 2008-156342 A | | 7/2008 | |
| JP | 2012-12351 A | | 1/2012 | |
| JP | 5247127 B2 | | 7/2013 | |
| JP | 2016-108243 A | | 6/2016 | |
| JP | 6469426 B2 | | 2/2019 | |
| JP | 2019-85390 A | | 6/2019 | |
| WO | WO 2015/136784 A1 | | 9/2015 | |

OTHER PUBLICATIONS

International Search Report issued Jan. 24, 2023 in PCT/JP2022/043247, filed on Nov. 22, 2022, 2 pages.
Kao, Japan, Day Barrier UV Protection Milk SPF 50+ PA+++, Mintel GNPD [online], Jun. 2021, Internet <URL : https://portal.mintel.com>, ID#8770763, [retrieved on Jan. 4, 2023] (with machine translation), 8 pages.
Kao, Japan, Vital Rich Cream (for dry skin), Mintel GNPD [online], Oct. 2002, Internet <URL : https://portal.mintel.com>, ID#173433, [retrieved on Jan. 10, 2023] (with machine translation), 4 pages.
Kao, USA, Dry Skin Therapy Hydra Silk Moisturizer, Mintel GNPD [online], Nov. 2019, ID#6996295, [retrieved on Jun. 6, 2023], Internet <URL : https://portal.mintel.com> (with machine translation), 6 pages.
Avon, Poland, Retroactive Plus Day Defence Lotion, Mintel GNPD [online], Nov.年 2005月, ID#416963, [retrieved on Jun. 6, 2023], Internet <URL : https://portal.mintel.com> (with machine translation), 6 pages.

* cited by examiner

*Primary Examiner* — Bethany P Barham
(74) *Attorney, Agent, or Firm* — Oblon, McClelland, Maier & Neustadt, L.L.P.

(57) ABSTRACT

An emulsion composition containing the following components (A), (B), (C), (D), and (E): (A) 0.1 to 20 mass % of an oil component having a melting point of from 50 to 150° C., (B) 1 to 30 mass % of octamethyltrisiloxane, (C) 1 to 20 mass % of an α-olefin oligomer, (D) a nonionic surfactant, and (E) water.

20 Claims, No Drawings

EMULSION COMPOSITION

CROSS REFERENCE TO RELATED APPLICATIONS

This application is a National Stage entry under 35 U.S.C. § 371 of PCT/JP2022/043247, filed on Nov. 22, 2022, and claims priority to Japanese Patent Application No. 2021-192526, filed on Nov. 26, 2021. The entire contents of both are incorporated herein by reference.

FIELD OF THE INVENTION

The present invention relates to an emulsion composition.

BACKGROUND OF THE INVENTION

Emulsion compositions containing solid lipids having a high melting point, such as ceramides, have stability problems such as crystal deposition or separation, though expected to have a high moisturizing effect. For example, an emulsion containing ceramides, a phospholipid derivative, fatty acid dextrin, and polyglycerin fatty acid ester (Patent Literature 1) has been studied.

And, improvement not only in stability of ceramides but also in water occlusive properties of the skin after application or use impression has been studied.

For example, Patent Literature 2 states that a water-in-oil emulsion composition containing ceramides, polyglycerin fatty acid ester, a specific lipophilic surfactant, dextrin fatty acid ester, a hydrocarbon oil which is in a liquid state at 25° C., and water has high water occlusive properties of a coating film and has favorable protective feeling or glossy feeling of the skin. Patent Literature 3 states that an emulsified cosmetic containing ceramides, meadowfoam estolide, cholesterol and/or phytosterol, a nonionic surfactant, an oil agent (except for meadowfoam estolide, cholesterol, and phytosterol), and water is excellent in usability without stickiness while stably containing the ceramides.

(Patent Literature 1) JP-A-2008-156342

(Patent Literature 2) JP-A-2019-85390

(Patent Literature 3) JP-A-2016-108243

SUMMARY OF THE INVENTION

The present invention relates to an emulsion composition comprising the following components (A), (B), (C), (D), and (E):

(A) 0.1 to 20 mass % of an oil component having a melting point of from 50 to 150° C.;

(B) 1 to 30 mass % of octamethyltrisiloxane;

(C) 1 to 20 mass % of an α-olefin oligomer;

(D) a nonionic surfactant; and (E) water.

DETAILED DESCRIPTION OF THE INVENTION

A low-temperature and low-humidity environment requires moisturizing the skin because the skin easily becomes dry. Hence, the skin can be rendered moist and fresh by applying an emulsified composition which contains solid lipids having a high melting point, such as ceramides, and has a high moisturizing effect to the skin, and thereby enhancing moist feeling of the skin in a sustained manner.

On the other hand, there are many people who suffer from dry skin even in summer, in an environment where the people frequently move between a hot and humid outdoor condition and an air-conditioned room with a low humidity, such as summer in Japan. For such people, it is preferred to apply an emulsified skincare agent which contains solid lipids having a high melting point, such as ceramides, and has a high moisturizing effect to the skin even in summer in order to render the skin moist and fresh by enhancing moist feeling of the skin in a sustained manner in an air-conditioned environment with a low humidity. However, people who put on such a conventional emulsified skincare agent sometimes experience an unpleasant feeling as if sizzling heat stagnates on the skin, when going outside in hot and humid weather. Hence, use of the conventional emulsified skincare agent containing solid lipids having a high melting point, such as ceramides, albeit having a high skincare effect, is not desired for people who suffer from dry skin in a state where the people frequently move between a hot and humid ambient environment in summer and an air-conditioned room with a low humidity in summer.

The present invention relates to an emulsion composition which contains solid lipid(s) having a high melting point, and has a high moisturizing effect of sustaining moist feeling of the skin and imparting moist and fresh feeling to the skin, while the emulsion composition does not offer an unpleasant feeling as if sizzling heat stagnates on the skin even in a hot and humid environment.

The present inventors found that an emulsion composition that can solve the problems described above can be obtained by combining an oil component having a specific melting point, octamethyltrisiloxane, an α-olefin oligomer, a nonionic surfactant, and water.

The emulsion composition of the present invention can stably contain an oil component having a high melting point, such as ceramides, sustains moist feeling while keeping moist and fresh feeling of the skin after application, reduces heat sensation even in a hot and humid environment, and can consequently reduce burdens on the skin.

The heat sensation refers to a feeling as if heat stagnates on the skin exposed to a hot and humid condition at or above a certain level in the state of the skin given the composition.

The component (A) used in the present invention is an oil component having a melting point of from 50 to 150° C. and is an oil component which is in a solid state at ordinary temperature (from 5 to 35° C.). Examples of such an oil component include: sphingolipids such as ceramides and sphingosines (including natural products and synthetic products); sterols such as cholesterol, dehydrocholesterol, β-sitosterol, stearoyl cholesteryl ester, isostearoyl cholesteryl ester, and vegetable oil fatty acid cholesteryl ester, and their related compounds; $C_{16}$-$C_{22}$ fatty acids such as stearic acid and behenic acid; and $C_{16}$-$C_{22}$ higher alcohols such as cetyl alcohol, stearyl alcohol, behenyl alcohol, batyl alcohol, and chimyl alcohol, and their related compounds. The component (A) is usually a component which is not defined as a surfactant, and is a component different from the component (D). The component (A) is a component which is not the α-olefin oligomer as the component (C), i.e., a hydrogenated polymer of linear aliphatic α-olefins having 4 to 12 carbon atoms.

Examples of the ceramides include natural ceramide and sphingosine derivatives as well as ceramide-like structural substances described in JP-A-62-228048, JP-A-63-216812, JP-A-63-227513, JP-A-64-29347, JP-A-64-31752, JP-A-8-319263, and the like. Specifically, a compound selected from the group consisting of compounds of the following formulas (1) and (2) is preferred, and a compound of the formula (1) is particularly preferred, from the viewpoint of improving sleek appearance, improving easiness to spread, improving moist feeling of the skin after application, and reducing burdens on the skin by reducing heat sensation in a hot and humid condition.

(1)

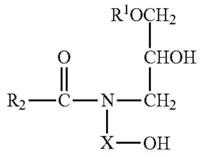

[In this formula, $R^1$ represents a hydrocarbon group having 10 to 26 carbon atoms, $R^2$ represents a hydrocarbon group having 9 to 25 carbon atoms, and X represents $-(CH_2)_n-$ (wherein n represents an integer of from 2 to 6)]

(2)

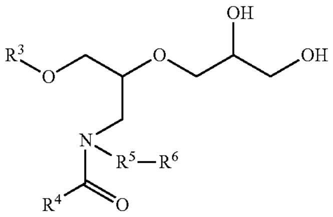

[In this formula, $R^3$ and $R^4$ are the same or different and each represent an optionally hydroxylated hydrocarbon group having 1 to 40 carbon atoms, $R^5$ represents an alkylene group having 1 to 6 carbon atoms or a single bond, and $R^6$ represents a hydrogen atom, an alkoxy group having 1 to 12 carbon atoms, or a 2,3-dihydroxypropyloxy group, provided that when $R^5$ is a single bond, $R^6$ is a hydrogen atom.]

In the formulas (1) and (2), the hydrocarbon group is preferably an alkyl group or an alkenyl group.

Examples of the compound of the formula (1) include N-(hexadecyloxyhydroxypropyl)-N-hydroxyethylhexadecanamide (INCI name: Cetyl-PG Hydroxyethyl Palmitamide). Examples of the compound of the formula (2) include long-chain dibasic acid-bis-3-methoxypropylamide.

The compound of the formula (1) is a pseudo-ceramide and is a ceramide functional component, which can complement ceramide functions and improve the state of the skin (moisture content and the like).

The component (A) preferably contains one or more selected from the group consisting of ceramides (particularly, natural ceramide, sphingosines, and compounds of the formulas (1) and (2)), $C_{16}$-$C_{22}$ fatty acids, and $C_{16}$-$C_{22}$ higher alcohols from the viewpoint of improving stability at a high temperature, improving sleek appearance, improving easiness to spread, improving moist feeling of the skin after application, improving sustained moist feeling of the skin after application, and reducing burdens on the skin by reducing heat sensation in a hot and humid condition, more preferably contains one or more selected from the group consisting of ceramides and $C_{16}$-$C_{22}$ higher alcohols, further more preferably contains a ceramide from the viewpoint of improving stability at a high temperature, improving sustained moist feeling of the skin after application, and reducing burdens on the skin by reducing heat sensation in a hot and humid condition, even more preferably contains one or more compounds selected from the group consisting of compounds of the formulas (1) and (2) which reduce burdens on the skin by reducing heat sensation in a hot and humid condition, even more preferably contains a compound of the formula (1), and especially preferably contains N-(hexadecyloxyhydroxypropyl)-N-hydroxyethylhexadecanamide.

The component (A) is preferably one or more selected from the group consisting of ceramides (particularly, natural ceramide, sphingosines, and compounds of the formulas (1) and (2)), $C_{16}$-$C_{22}$ fatty acids, and $C_{16}$-$C_{22}$ higher alcohols from the viewpoint of improving stability at a high temperature, improving sleek appearance, improving easiness to spread, improving moist feeling of the skin after application, improving sustained moist feeling of the skin after application, and reducing burdens on the skin by reducing heat sensation in a hot and humid condition, more preferably one or more selected from the group consisting of ceramides and $C_{16}$-$C_{22}$ higher alcohols, further more preferably a ceramide from the viewpoint of improving stability at a high temperature, improving sustained moist feeling of the skin after application, and reducing burdens on the skin by reducing heat sensation in a hot and humid condition, even more preferably one or more compounds selected from the group consisting of compounds of the formulas (1) and (2) from the viewpoint of reducing burdens on the skin by reducing heat sensation in a hot and humid condition, especially preferably a compound of the formula (1), especially preferably N-(hexadecyloxyhydroxypropyl)-N-hydroxyethylhexadecanamide.

When the component (A) contains a ceramide, a $C_{16}$-$C_{22}$ fatty acid, and a $C_{16}$-$C_{22}$ higher alcohol, a total content ratio of the ceramide, the $C_{16}$-$C_{22}$ fatty acid, and the $C_{16}$-$C_{22}$ higher alcohol to the component (A) is preferably from 20 to 100 mass %, more preferably from 30 to 100 mass %, further more preferably from 50 to 100 mass %, even more preferably from 75 to 100 mass %, especially preferably from 85 to 100 mass %, most preferably substantially 100 mass %, in the component (A) from the viewpoint of improving stability at a high temperature, improving sleek appearance, improving easiness to spread, improving moist feeling of the skin after application, improving sustained moist feeling of the skin after application, and reducing burdens on the skin by reducing heat sensation in a hot and humid condition.

When the component (A) contains a ceramide, a content ratio of the ceramide to the component (A) is preferably from 20 to 100 mass %, more preferably from 30 to 100 mass %, further more preferably from 50 to 100 mass %, even more preferably from 75 to 100 mass %, especially preferably from 85 to 100 mass %, most preferably substantially 100 mass %, in the component (A) from the viewpoint of improving stability at a high temperature, improving sustained moist feeling after application, and reducing burdens on the skin by reducing heat sensation in a hot and humid condition.

When the component (A) contains one or more compounds selected from the group consisting of compounds of the formulas (1) and (2), a content ratio of the one or more compounds selected from the group consisting of compounds of the formulas (1) and (2) to the component (A) is preferably from 20 to 100 mass %, more preferably from 30 to 100 mass %, further more preferably from 50 to 100 mass %, even more preferably from 75 to 100 mass %, especially preferably from 85 to 100 mass %, most preferably substantially 100 mass %, in the component (A) from the viewpoint of further reducing burdens on the skin by reducing heat sensation in a hot and humid condition.

When the component (A) contains N-(hexadecyloxyhydroxypropyl)-N-hydroxyethylhexadecanamide, a content ratio of the N-(hexadecyloxyhydroxypropyl)-N-hydroxyethylhexadecanamide to the component (A) is preferably from 20 to 100 mass %, more preferably from 30 to 100 mass %, further more preferably from 50 to 100 mass %, even more preferably from 75 to 100 mass %, especially preferably from 85 to 100 mass %, most preferably substantially 100 mass %, in the component (A) from the viewpoint of further reducing burdens on the skin by reducing heat sensation in a hot and humid condition.

When the component (A) contains a ceramide, a $C_{16}$-$C_{22}$ fatty acid, and a $C_1$-$C_{22}$ higher alcohol, a total content ratio of the $C_{16}$-$C_{22}$ fatty acid and the $C_{16}$-$C_{22}$ higher alcohol to a total amount of the ceramide, the $C_{16}$-$C_{22}$ fatty acid, and the $C_{16}$-$C_{22}$ higher alcohol in the component (A) is preferably 90 mass % or less, more preferably 70 mass % or less, further more preferably 50 mass % or less, even more preferably 25 mass % or less, especially preferably 10 mass % or less, most preferably substantially 0 mass %, from the viewpoint of improving stability at a high temperature.

When the component (A) contains a ceramide and a $C_{16}$-$C_{22}$ fatty acid, a total content ratio of the $C_{16}$-$C_{22}$ fatty acid to a total amount of the ceramide and the $C_{16}$-$C_{22}$ fatty acid in the component (A) is preferably 90 mass % or less, more preferably 70 mass % or less, further more preferably 50 mass % or less, even more preferably 25 mass % or less, especially preferably 10 mass % or less, most preferably substantially 0 mass %, from the viewpoint of improving stability at a high temperature.

When the component (A) contains a ceramide and a $C_{16}$-$C_{22}$ higher alcohol, a total content ratio of the $C_{16}$-$C_{22}$ higher alcohol to a total amount of the ceramide and the $C_{16}$-$C_{22}$ higher alcohol in the component (A) is preferably 90 mass % or less, more preferably 70 mass % or less, further more preferably 50 mass % or less, even more preferably 25 mass % or less, especially preferably 10 mass % or less, most preferably substantially 0 mass %, from the viewpoint of improving stability at a high temperature.

When the component (A) contains N-(hexadecyloxyhydroxypropyl)-N-hydroxyethylhexadecanamide, a $C_{16}$-$C_{22}$ fatty acid, and a $C_{16}$-$C_{22}$ higher alcohol, a total content ratio of the $C_{16}$-$C_{22}$ fatty acid and the $C_{16}$-$C_{22}$ higher alcohol to a total amount of the N-(hexadecyloxyhydroxypropyl)-N-hydroxyethylhexadecanamide, the $C_{16}$-$C_{22}$ fatty acid, and the $C_{16}$-$C_{22}$ higher alcohol in the component (A) is preferably 90 mass % or less, more preferably 70 mass % or less, further more preferably 50 mass % or less, even more preferably 25 mass % or less, especially preferably 10 mass % or less, most preferably substantially 0 mass %, from the viewpoint of improving stability at a high temperature.

One of or a combination of two or more of these oil components can be used as the component (A), and a content thereof is 0.1 mass % or more, preferably 2 mass % or more, more preferably 5 mass % or more, and 20 mass % or less, preferably 15 mass % or less, more preferably 9 mass % or less, in the entire composition from the viewpoint of improving stability at room temperature and at a high temperature, improving easiness to spread, improving moist feeling of the skin after application, improving sustained moist feeling, and reducing heat sensation. The content of the component (A) is from 0.1 to 20 mass %, preferably from 2 to 15 mass %, more preferably from 5 to 9 mass %, in the entire composition.

The octamethyltrisiloxane (trisiloxane) as the component (B) is a compound of the following formula and is a silicone oil whose viscosity at 25° C. is approximately 1 cs.

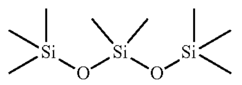

The viscosity of the component (B) is measured under conditions of 25° C., a rotational speed of 12 rpm, a measurement time of 60 seconds, and rotor No. 1 using a type B viscometer (model TVB10 viscometer, manufactured by Toki Sangyo Co., Ltd.).

A content of the component (B) is 1 mass % or more, preferably 1.5 mass % or more, more preferably 2 mass % or more, further more preferably 5 mass % or more, and 30 mass % or less, preferably 20 mass % or less, more preferably 13 mass % or less, further more preferably 8.5 mass % or less, in the entire composition from the viewpoint of improving sleek appearance, improving easiness to spread, improving moist feeling of the skin after application, improving sustained moist feeling of the skin after application, and reducing burdens on the skin by reducing heat sensation in a hot and humid condition. The content of the component (B) is from 1 to 30 mass %, preferably from 1.5 to 20 mass %, more preferably from 2 to 13 mass %, further more preferably from 5 to 8.5 mass %, in the entire composition The α-olefin oligomer as the component (C) is a hydrogenated polymer of linear aliphatic α-olefins having 4 to 12 carbon atoms. The component (C) according to the present invention is a component different from the oil component (A) having a melting point of from 50 to 150° C.

A molecular weight of the α-olefin oligomer as the component (C) is preferably 300 or more, more preferably 330 or more, further more preferably 360 or more, even more preferably 400 or more, and preferably 800 or less, more preferably 700 or less, further more preferably 600 or less, even more preferably 500 or less, from the viewpoint of improving sleek appearance, improving moist feeling of the skin after application, improving sustained moist feeling of the skin after application, and reducing burdens on the skin by reducing heat sensation in a hot and humid condition. The molecular weight of the α-olefin oligomer as the component (C) is preferably from 300 to 800, more preferably from 330 to 700, further more preferably from 360 to 600, even more preferably from 400 to 500.

In this context, the molecular weight of the component (C) is a weight-average molecular weight and can be measured by SEC analysis on a polystyrene basis.

A viscosity at 25° C. of the α-olefin oligomer as the component (C) is preferably 5 mPa·s or more, more preferably 8 mPa·s or more, further more preferably 12 mPa·s or more, even more preferably 15 mPa·s or more, and preferably 50 mPa·s or less, more preferably 45 mPa·s or less, further more preferably 30 mPa·s or less, even more preferably 25 mPa·s or less, from the viewpoint of improving sleek appearance, improving moist feeling of the skin after application, improving sustained moist feeling of the skin after application, and reducing burdens on the skin by reducing heat sensation in a hot and humid condition. The viscosity at 25° C. of the α-olefin oligomer as the component (C) is preferably from 5 to 50 mPa·s, more preferably from 8 to 45 mPa·s, further more preferably from 12 to 30 mPa·s, even more preferably from 15 to 25 mPa·s.

The viscosity at 25° C. is measured under conditions of a rotational speed of 12 rpm, a measurement time of 60 seconds, and rotor No. 1 using a type B viscometer (model TVB10 viscometer, manufactured by Toki Sangyo Co., Ltd.).

An olefin moiety of the α-olefin oligomer as the component (C) is a hydrogenated polymer of linear aliphatic α-olefins having 4 to 12 carbon atoms, preferably linear aliphatic α-olefins having 6 to 12 carbon atoms, more preferably linear aliphatic α-olefins having 8 to 12 carbon atoms, further more preferably linear aliphatic α-olefins having 10 carbon atoms. The olefin moiety may be a polymer of linear aliphatic α-olefins having a single number of carbon atoms or may be composed of linear aliphatic α-olefins having different numbers of carbon atoms by the polymerization of the linear aliphatic α-olefins having different numbers of carbon atoms as long as the linear aliphatic α-olefins have 4 to 12 carbon atoms. A polymer of linear aliphatic α-olefins having a single number of carbon atoms is preferred.

The α-olefin oligomer as the component (C) is a polymer of linear aliphatic α-olefins having 4 to 12 carbon atoms, and a degree of polymerization is preferably from 3 to 6, more preferably from 3 to 4, from the viewpoint of improving sustained moist feeling of the skin after application, and reducing burdens on the skin by reducing heat sensation in a hot and humid condition. As for the degree of polymerization, the component (C) may be composed of a component having a single degree of polymerization or may be composed of components having different degrees of polymerization. In general, the component (C) is preferably composed of components having different degrees of polymerization from the viewpoint of improving moist feeling of the skin after application, improving sustained moist feeling of the skin after application, and reducing burdens on the skin by reducing heat sensation in a hot and humid condition.

In this context, the degree of polymerization of the component (C) is calculated by dividing the value of the weight-average molecular weight by a molecular weight of a monomer. When the monomer is constituted by a plurality of molecules, the degree of polymerization is calculated by dividing the value by an average molecular weight of the monomer.

Monomer species constituting the α-olefin oligomer and a compositional ratio thereof can be determined by general instrumental analysis and can be determined by, for example, GC-MS or LC-MS, or NMR in addition to GC-MS or LC-MS. The average molecular weight of the monomer is calculated from the monomer species and the compositional ratio based on the measurement results.

A constituent ratio of components having the degree of polymerization of from 3 to 4 in the component (C) is preferably 50 mass % or more, more preferably 65 mass % or more, further more preferably 80 mass % or more, even more preferably substantially 100 mass %, in the component (C) from the viewpoint of improving sustained moist feeling of the skin after application, and reducing burdens on the skin by reducing heat sensation in a hot and humid condition.

A constituent ratio of components having the degree of polymerization of 5 or more in the component (C) is preferably less than 50 mass %, more preferably less than 35 mass %, further more preferably less than 20 mass %, even more preferably substantially zero, in the component (C) from the viewpoint of improving sustained moist feeling of the skin after application, and reducing burdens on the skin by reducing heat sensation in a hot and humid condition.

For example, a commercially available product such as "SILKFLO 364 (molecular weight: 444, viscosity at 25° C.: 23.7 mPa·s)" or "SILKFLO 366 (molecular weight: 556, viscosity at 25° C.: 43.6 mPa·s)" (both manufactured by Vantage Specialty Chemicals) can be used as the α-olefin oligomer as the component (C).

A content of the component (C) is 1 mass % or more, preferably 2 mass % or more, further more preferably 4 mass % or more, and 20 mass % or less, preferably 13 mass % or less, more preferably 8 mass % or less, in the entire composition from the viewpoint of improving sleek appearance, improving easiness to spread, improving sustained moist feeling of the skin after application, and reducing heat sensation. The content of the component (C) is from 1 to 20 mass %, preferably from 2 to 13 mass %, more preferably from 4 to 8 mass %, in the entire composition.

In the present invention, a mass ratio of the component (A) to the component (B), (A)/(B), is preferably 0.1 or more, more preferably 0.38 or more, further more preferably 0.6 or more, even more preferably 1 or more, especially preferably 1.08 or more, and preferably 10 or less, more preferably 5 or less, further more preferably 3.3 or less, even more preferably 1.9 or less, especially preferably 1.4 or less, from the viewpoint of improving sleek appearance, improving easiness to spread, improving moist feeling of the skin after application, improving sustained moist feeling of the skin after application, and reducing burdens on the skin by reducing heat sensation in a hot and humid condition. The mass ratio of the component (A) to the component (B), (A)/(B), is preferably from 0.1 to 10, more preferably from 0.38 to 5, further more preferably from 0.6 to 3.3, even more preferably from 1 to 1.9, especially preferably from 1.08 to 1.4.

In the present invention, a mass ratio of the component (A) to the component (C), (A)/(C), is preferably 0.1 or more, more preferably 0.4 or more, further more preferably 0.67 or more, even more preferably 1.1 or more, and preferably 10 or less, more preferably 5 or less, further more preferably 3.3 or less, even more preferably 2.1 or less, from the viewpoint of improving sleek appearance, improving easiness to spread, improving moist feeling of the skin after application, and improving sustained moist feeling of the skin after application. The mass ratio of the component (A) to the component (C), (A)/(C), is preferably from 0.1 to 10, more preferably from 0.4 to 5, further more preferably from 0.67 to 3.3, even more preferably from 1.1 to 2.1.

In the present invention, a mass ratio of the component (B) to the component (C), (B)/(C), is preferably 0.1 or more, more preferably 0.48 or more, further more preferably 0.6 or more, even more preferably 0.8 or more, especially preferably 0.93 or more, and preferably 10 or less, more preferably 5 or less, further more preferably 3.3 or less, even more preferably 1.8 or less, especially preferably 1.47 or less, from the viewpoint of improving sleek appearance, improving easiness to spread, improving moist feeling of the skin after application, improving sustained moist feeling of the skin after application, and reducing burdens on the skin by reducing heat sensation in a hot and humid condition. The mass ratio of the component (B) to the component (C), (B)/(C), is preferably from 0.1 to 10, more preferably from 0.48 to 5, further more preferably from 0.6 to 3.3, even more preferably from 0.8 to 1.8, especially preferably from 0.93 to 1.47.

The component (D) is a nonionic surfactant, and a known one can be used. The component (D) of the present invention is a component different from the oil component (A) having a melting point of from 50 to 150° C.

Specific examples thereof include polyglycerin fatty acid ester, glycerin fatty acid ester, propylene glycol fatty acid ester, sorbitan fatty acid ester, polyoxyethylene sorbitan fatty acid ester, polyoxyethylene castor oil, polyoxyethylene hydrogenated castor oil, polyoxyethylene hydrogenated castor oil fatty acid ester, polyethylene glycol fatty acid ester, alkyl glyceryl ether, alkyl polyglyceryl ether, polyoxyethylene alkyl ether, polyoxyethylene alkyl ether fatty acid ester, polyoxyethylene alkylamine, and silicone-based surfactants.

Examples of the polyoxyethylene sorbitan fatty acid ester include polyoxyethylene sorbitan fatty acid ester in which an average number of moles of added polyoxyethylene chains constituting it is from 10 to 20, and specifically include polyoxyethylene sorbitan monostearate (20E.O.).

Examples of the polyoxyethylene hydrogenated castor oil include polyoxyethylene hydrogenated castor oil in which an average number of moles of added polyoxyethylene chains constituting it is from 10 to 100, and specifically include PEG-10 hydrogenated castor oil.

Examples of the polyoxyethylene hydrogenated castor oil fatty acid ester include polyoxyethylene hydrogenated castor oil fatty acid ester in which an average number of moles of added polyoxyethylene chains constituting it is from 10 to 100, and specifically include PEG-15 hydrogenated castor oil isostearate.

Specific examples of the alkyl glyceryl ether include 2-ethylhexyl glyceryl ether, isododecyl glyceryl ether, and isostearyl glyceryl ether.

Specific examples of the silicone-based surfactant include polyether-modified silicone such as PEG-3 dimethicone, PEG-10 dimethicone, and PEG-12 dimethicone, polyether/alkyl co-modified silicone, polyglycerin-modified silicone, polyglycerin/alkyl co-modified silicone, and alkyl silicone dendron polyether-modified silicone.

Other examples of the silicone-based surfactant include silicone-based surfactants having a linear or branched backbone silicone chain and also include silicone-based surfactants having a cross-linked or non-cross-linked silicone chain.

The component (D) preferably contains at least one selected from the group consisting of a silicone-based surfactant, polyoxyethylene hydrogenated castor oil, alkyl glyceryl ether, and sorbitan fatty acid ester, more preferably contains at least one selected from the group consisting of a silicone-based surfactant, polyoxyethylene hydrogenated castor oil, and alkyl glyceryl ether, and further more preferably contains at least one selected from the group consisting of alkyl glyceryl ether and a silicone-based surfactant, from the viewpoint of forming a stable water-in-oil emulsion composition and from the viewpoint of improving stability at a high temperature, improving easiness to spread, improving moist feeling of the skin after application, and reducing burdens on the skin by reducing heat sensation in a hot and humid condition.

In the polyoxyethylene hydrogenated castor oil, the average number of moles of added polyoxyethylene chains constituting the polyoxyethylene hydrogenated castor oil is preferably from 10 to 100, more preferably from 10 to 60, further more preferably from 10 to 40, even more preferably from 10 to 20, especially preferably 10.

The sorbitan fatty acid ester is preferably sorbitan monostearate.

The alkyl glyceryl ether is preferably one or more selected from the group consisting of 2-ethylhexyl glyceryl ether, isododecyl glyceryl ether, and isostearyl glyceryl ether, more preferably isostearyl glyceryl ether.

The silicone-based surfactant is preferably at least one selected from the group consisting of polyether-modified silicone, polyglycerin-modified silicone, polyether/alkyl co-modified silicone, and polyglycerin/alkyl co-modified silicone, more preferably at least one selected from the group consisting of polyether-modified silicone and polyether/alkyl co-modified silicone, further more preferably polyether-modified silicone, even more preferably polyether-modified silicone having a linear backbone silicone chain, especially preferably at least one selected from the group consisting of PEG-3 dimethicone, PEG-10 dimethicone, and PEG-12 dimethicone, preferably at least one selected from the group consisting of PEG-3 dimethicone and PEG-12 dimethicone.

The component (D) preferably contains alkyl glyceryl ether and a silicone-based surfactant at the same time. When the component (D) contains alkyl glyceryl ether and a silicone-based surfactant at the same time, the component (D) preferably contains isostearyl glyceryl ether and polyether-modified silicone, more preferably contains isostearyl glyceryl ether and one or more selected from the group consisting of PEG-3 dimethicone, PEG-10 dimethicone, and PEG-12 dimethicone, further more preferably contains isostearyl glyceryl ether and one or more selected from the group consisting of PEG-3 dimethicone and PEG-12 dimethicone, and even more preferably contains isostearyl glyceryl ether and PEG-3 dimethicone, from the viewpoint of forming a stable water-in-oil emulsion composition and from the viewpoint of improving stability at a high temperature, improving easiness to spread, improving moist feeling of the skin after application, and reducing burdens on the skin by reducing heat sensation in a hot and humid condition.

The component (D) preferably contains at least one selected from the group consisting of a silicone-based surfactant, sorbitan fatty acid ester, polyoxyethylene sorbitan fatty acid ester, polyoxyethylene hydrogenated castor oil, and polyoxyethylene hydrogenated castor oil fatty acid ester, more preferably contains at least one selected from the group consisting of sorbitan fatty acid ester, polyoxyethylene sorbitan fatty acid ester, and polyoxyethylene hydrogenated castor oil, and further more preferably contains at least one selected from the group consisting of sorbitan fatty acid ester and polyoxyethylene sorbitan fatty acid ester, from the viewpoint of forming a stable oil-in-water emulsion composition and from the viewpoint of improving stability at a high temperature, improving easiness to spread, improving moist feeling of the skin after application, and reducing burdens on the skin by reducing heat sensation in a hot and humid condition.

The sorbitan fatty acid ester is preferably sorbitan monostearate.

The polyoxyethylene sorbitan fatty acid ester is preferably polyoxyethylene sorbitan fatty acid ester in which an average number of moles of added polyoxyethylene chains constituting it is from 10 to 20 and more preferably 20, further more preferably polyoxyethylene sorbitan monostearate (20E.O.).

The polyoxyethylene hydrogenated castor oil is polyoxyethylene hydrogenated castor oil in which an average number of moles of added polyoxyethylene chains constituting it is preferably from 20 to 100, more preferably from 40 to 80, further more preferably from 50 to 60.

The polyoxyethylene hydrogenated castor oil fatty acid ester is polyoxyethylene hydrogenated castor oil fatty acid ester in which an average number of moles of added polyoxyethylene chains constituting it is preferably from 20 to 100, more preferably from 40 to 80, further more preferably from 50 to 60.

The nonionic surfactant as the component (D) has a HLB value of preferably from 1 to 7, more preferably from 1 to 6, further more preferably from 2 to 6, from the viewpoint of not impairing water resistance against sweat upon application in a hot and humid condition, from the viewpoint of forming a stable water-in-oil emulsion composition, and from the viewpoint of improving stability at room temperature and at a high temperature, when the emulsion composition is a water-in-oil emulsion composition. In this context, when the component (D) is constituted by two or more surfactants, both of their HLB values are preferably from 1 to 7, more preferably from 1 to 6, further more preferably from 2 to 6, from the viewpoint of not impairing water resistance against sweat upon application in a hot and humid condition, from the viewpoint of forming a stable water-in-oil emulsion composition, and from the viewpoint of improving stability at a high temperature.

The nonionic surfactant as the component (D) has a HLB value of preferably from 8 to 18, more preferably from 8 to 16, further more preferably from 8 to 14, from the viewpoint of forming a stable oil-in-water emulsion composition when the emulsion composition is an oil-in-water emulsion composition. In this context, when the component (D) is constituted by two or more surfactants, both of their HLB values are preferably from 8 to 18, more preferably from 8 to 16, further more preferably from 8 to 14, from the viewpoint of forming a stable oil-in-water emulsion composition, and from the viewpoint of improving stability at a high temperature.

In this context, the HLB (hydrophilic-lipophilic balance) refers to a molecular weight of a hydrophilic moiety to the total molecular weight of the surfactant, and is determined according to the equation of Griffin. When the component (D) is constituted by two or more nonionic surfactants, HLB of the surfactant mixture is determined as follows: the HLB of the surfactant mixture is an arithmetic average value of the respective HLB values of the nonionic surfactants based on a compositional ratio thereof.

$$\text{Mixed HLB}=\Sigma(\text{HLB}x\times Wx)/\Sigma Wx$$

HLBx represents a HLB value of a nonionic surfactant X.

Wx represents a mass (g) of the nonionic surfactant X having the HLBx value.

For example, a commercially available product such as "PENETOL GE-IS (HLB: 2)" (manufactured by Kao Corp.) as isostearyl glyceryl ether, PEG-3 dimethicone "KF-6015 (HLB: 4.5)", PEG-11 methyl ether dimethicone "KF-6011 (HLB: 14.5)", "KF-6011P (HLB: 14.5)", PEG-10 dimethicone "KF-6043 (HLB: 14.5)", "Silicone KF-6017 (HLB: 4.5)", PEG-9 polydimethylsiloxyethyl dimethicone "Silicone KF-6028 (HLB: 4.0)" (all manufactured by Shin-Etsu Chemical Co., Ltd.); PEG-12 dimethicone "SH-3775M (HLB: 5)", "SH-3771M (HLB: 13)", "SS-2804 (HLB: 13)", PEG/PPG-19/19 dimethicone-cyclopentasiloxane mixture "Silicone BY11-030 (HLB: 3.0)", "Silicone BY22-008M (HLB: 2.0)" (all manufactured by Dow Corning Toray Silicone Co., Ltd.), or the like as polyether-modified silicone, or PEG-5 hydrogenated castor oil "EMALEX HC-5 (HLB: 5.0)" (Nihon Emulsion Co., Ltd.), PEG-10 hydrogenated castor oil "NIKKOL HCO-10 (HLB 6.5)" (manufactured by Nippon Surfactant Industries, Co., Ltd.), or PEG-15 hydrogenated castor oil triisostearate "EMALEX RWIS-315 (HLB: 5.0)" (Nihon Emulsion Co., Ltd.) as polyoxyethylene hydrogenated castor oil can be used as the nonionic surfactant as the component (D).

One or more nonionic surfactants can be used as the component (D), and a content thereof is preferably 0.1 mass % or more, more preferably 0.5 mass % or more, further more preferably 1 mass % or more, even more preferably 1.5 mass % or more, and preferably 8 mass % or less, more preferably 5 mass % or less, further more preferably 3.5 mass % or less, even more preferably 3 mass % or less, in the entire composition from the viewpoint of forming a stable emulsion composition and from the viewpoint of improving stability at room temperature and at a high temperature. The content of the component (D) is preferably from 0.1 to 8 mass %, more preferably from 0.5 to 5 mass %, further more preferably from 1 to 3.5 mass %, even more preferably from 1.5 to 3 mass %, in the entire composition.

In the present invention, the content of the water as the component (E) is preferably 10 mass % or more, more preferably 15 mass % or more, further more preferably 20 mass % or more, and preferably 85 mass % or less, more preferably 75 mass % or less, further more preferably 70 mass % or less, in the entire composition from the viewpoint of forming a stable water-in-oil emulsion composition and from the viewpoint of improving moist feeling of the skin after application. The content of the water as the component (E) is preferably from 10 to 85 mass %, more preferably from 15 to 75 mass %, further more preferably from 20 to 70 mass %, in the entire composition.

The emulsion composition of the present invention preferably further contains a polyhydric alcohol and can improve moist feeling of the skin after application and improve sustained moist feeling of the skin after application.

The polyhydric alcohol is a compound having two or more hydroxy groups in the molecule and may not be limited as long as it can be used in usual cosmetics.

Examples of the dihydric alcohol include ethylene glycol, diethylene glycol, triethylene glycol, polyethylene glycol, propylene glycol, dipropylene glycol, tripropylene glycol, polypropylene glycol, 1,3-butylene glycol, and propanediol. Examples of the trihydric alcohol include glycerin and trimethylolpropane. Examples of the tetrahydric alcohol include diglycerin and erythritol. Examples of the pentahydric or higher polyhydric alcohol include: polyglycerin such as triglycerin; and sugars and sugar alcohols, such as glucose, maltose, maltitose, sucrose, xylitol, sorbitol, maltitol, polyoxyethylene methyl glucoside, polyoxyethylene ethyl glucoside, and polyoxyethylene propylene glucoside.

The polyhydric alcohol preferably contains one or more selected from the group consisting of at least a dihydric alcohol, a trihydric alcohol, a tetrahydric alcohol, and a sugar alcohol, more preferably contains one or more selected from the group consisting of at least a dihydric alcohol, a trihydric alcohol, and a tetrahydric alcohol, further more preferably contains one or more selected from the group consisting of at least propanediol, dipropylene glycol, 1,3-butylene glycol, glycerin, and diglycerin, even more preferably contains one or more selected from the group consisting of at least dipropylene glycol, 1,3-butylene glycol, and glycerin, and especially preferably contains at least glycerin, from the viewpoint of improving moist feeling of the skin after application, and improving sustained moist feeling of the skin after application.

One of or a combination of two or more of these polyhydric alcohols can be used, and a total content thereof is preferably 1 mass % or more, more preferably 5 mass % or more, further more preferably 10 mass % or more, and preferably 30 mass % or less, more preferably 20 mass % or less, further more preferably 15 mass % or less, in the entire composition from the viewpoint of improving moist feeling of the skin after application, and improving sustained moist feeling of the skin after application. The content of the polyhydric alcohol is preferably from 1 to 30 mass %, more preferably from 5 to 20 mass %, further more preferably from 10 to 15 mass %, in the entire composition.

The emulsion composition of the present invention preferably further contains an anionic surfactant and can form a stable oil-in-water emulsion composition, improve moist feeling of the skin after application, and improve sustained moist feeling of the skin after application.

The anionic surfactant may not be limited as long as it can be used in usual emulsion compositions. Examples thereof include: N-acyl amino acids including N-acylglutamic acid and salts thereof, such as N-lauroyl-L-glutamic acid, N-stearoyl-L-glutamic acid, and N-myristoyl-L-glutamic acid; N-acyl methyl taurine and salts thereof, such as N-myristoyl-N-methyl taurine, N-lauroyl-N-methyl taurine, and N-stearoyl-N-methyl taurine; and fatty acids and salts thereof.

The anionic surfactant preferably contains one or more selected from the group consisting of N-acylglutamic acid and a salt thereof, and N-acyl methyl taurine and a salt thereof, more preferably contains one or more selected from the group consisting of N-stearoyl-L-glutamic acid and a salt thereof, and N-stearoyl-N-methyl taurine and a salt thereof, and further more preferably contains one or more selected from the group consisting of sodium N-stearoyl-L-glutamate and sodium N-stearoyl-N-methyl taurine, from the viewpoint of forming a stable oil-in-water emulsion composition and from the viewpoint of improving moist feeling of the skin after application, and improving sustained moist feeling of the skin after application.

One of or a combination of two or more of these anionic surfactants can be used, and a total content thereof is preferably 0.1 mass % or more, more preferably 0.3 mass % or more, further more preferably 0.5 mass % or more, and preferably 5 mass % or less, more preferably 3 mass % or less, further more preferably 1 mass % or less, in the entire composition from the viewpoint of forming a stable oil-in-water emulsion composition and from the viewpoint of improving moist feeling of the skin after application, and improving sustained moist feeling of the skin after application. The content of the anionic surfactant is preferably from 0.1 to 5 mass %, more preferably from 0.3 to 3 mass %, further more preferably from 0.5 to 1 mass %, in the entire composition.

The emulsion composition of the present invention can contain, in addition to the components described above, a component which is usually used in formulations for external use, fragrance formulations, and cosmetics, for example, an active ingredient for medicaments or quasi-drugs, such as an oil component other than the components (A), (B), and (C), a surfactant other than the component (D) and an anionic surfactant, a powder, a UV protective agent other than a powder, a polymer compound, an antioxidant, a fragrance, an antiseptic, a pH adjuster, a blood circulation promoting agent, a cooling agent, an antiperspirant, a germicide, a skin activator, a moisturizing agent other than a polyhydric alcohol, a freshener, a skin lighting agent, an anti-wrinkle agent, an anti-inflammatory agent, a steroid agent, an immunosuppressant, or a molecular targeting drug.

In the emulsion composition of the present invention, a content of an insoluble powder in the emulsion composition, specifically, an inorganic powder, an organic-inorganic composite powder, or a surface-modified inorganic/organic powder, which is generally used as a coloring pigment or a UV scattering agent, is preferably 30 mass % or less, more preferably 20 mass % or less, further more preferably 10 mass % or less, even more preferably 5 mass % or less, especially preferably substantially zero, in the entire composition from the viewpoint of improving easiness to spread, improving sustained moist feeling of the skin after application, and reducing burdens on the skin by reducing heat sensation in a hot and humid condition. Also, a content of a UV protective agent other than a powder is preferably 20 mass % or less, more preferably 15 mass % or less, further more preferably 10 mass % or less, even more preferably 5 mass % or less, especially preferably substantially zero, in the entire composition from the viewpoint of improving easiness to spread, improving sustained moist feeling of the skin after application, and reducing burdens on the skin by reducing heat sensation in a hot and humid condition.

The emulsion composition of the present invention can be produced by a usual method.

The emulsion composition of the present invention can be prepared as any of a water-in-oil emulsion composition, an oil-in-water emulsion composition, and the like and is preferably a water-in-oil emulsion composition from the viewpoint of retaining water resistance against sweat in summer and from the viewpoint of improving sustained moist feeling after application.

The emulsion composition of the present invention can stably contain an oil component having a high melting point, such as ceramides, sustains moist feeling while keeping moist and fresh feeling of the skin after application, reduces heat sensation even in a hot and humid environment, and can consequently reduce burdens on the skin.

In addition to the effects described above, the resulting emulsion composition even has sleek appearance, is easy to spread upon application to the skin, produces smooth use impression, and secures high-temperature stability of a formulation capable of enduring use at a high temperature.

The emulsion composition of the present invention can be used as a cosmetic or a skin formulation for external use and is preferably used as a cosmetic. Examples of the dosage form of the emulsion composition of the present invention include creams and emulsions. A cream is preferred from the viewpoint of enhancing effects of the present invention. Specific examples of the cosmetic can include skincare emulsions for facial or body skin, skincare creams, BB creams, BB emulsions, serums, hand creams, lip care products, sunscreens, hair styling products, and hair conditioners. Among them, the cosmetic is preferably a skincare emulsion for facial or body skin, a skincare cream, a BB cream, a BB emulsion, a serum, a hand cream, or a lip care product, more preferably a skincare cream, from the viewpoint of sufficiently exerting effects of the present invention.

The emulsion composition of the present invention can be allowed to contain a UV scattering agent or a UV protective agent and thereby prepared as a sunscreen. A cosmetic except for a sunscreen is preferred from the viewpoint of improving easiness to spread, improving moist feeling of the skin after application, improving sustained moist feeling of the skin after application, and reducing burdens on the skin by reducing heat sensation in a hot and humid condition.

In relation to the embodiments mentioned above, the present invention further discloses the following composition and the like.

<1> An emulsion composition comprising the following components (A), (B), (C), (D), and (E):

(A) 0.1 to 20 mass % of an oil component having a melting point of from 50 to 150° C.;
(B) 1 to 30 mass % of octamethyltrisiloxane;
(C) 1 to 20 mass % of an α-olefin oligomer;
(D) a nonionic surfactant; and
(E) water.

<2> The emulsion composition according to <1>, wherein the component (A) is preferably one or more selected from the group consisting of ceramides (particularly, natural ceramide, sphingosines, and compounds of the formulas (1) and (2)), $C_{16}$-$C_{22}$ fatty acids, and $C_{16}$-$C_{22}$ higher alcohols, more preferably comprises one or more selected from the group consisting of ceramides and $C_{16}$-$C_{22}$ higher alcohols, further more preferably comprises a ceramide, even more preferably comprises one or more compounds selected from the group consisting of compounds of the formulas (1) and (2):

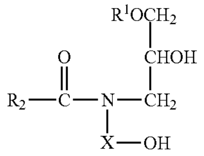

(1)

wherein $R^1$ represents a hydrocarbon group having 10 to 26 carbon atoms, $R^2$ represents a hydrocarbon group having 9 to 25 carbon atoms, and X represents $-(CH_2)_n-$ (wherein n represents an integer of from 2 to 6),

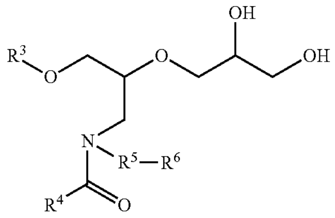

(2)

wherein $R^3$ and $R^4$ are the same or different and each represent an optionally hydroxylated hydrocarbon group having 1 to 40 carbon atoms, $R^5$ represents an alkylene group having 1 to 6 carbon atoms or a single bond, and $R^6$ represents a hydrogen atom, an alkoxy group having 1 to 12 carbon atoms, or a 2,3-dihydroxypropyloxy group, provided that when $R^5$ is a single bond, $R^6$ is a hydrogen atom, even more preferably comprises a compound of the formula (1), and especially preferably comprises N-(hexadecyloxyhydroxypropyl)-N-hydroxyethylhexadecanamide.

<3> The emulsion composition according to <1> or <2>, wherein the component (A) is preferably one or more selected from the group consisting of ceramides (particularly, natural ceramide, sphingosines, and compounds of the formulas (1) and (2)), $C_{16}$-$C_{22}$ fatty acids, and $C_{16}$-$C_{22}$ higher alcohols, more preferably one or more selected from the group consisting of ceramides and $C_{16}$-$C_{22}$ higher alcohols, further more preferably a ceramide, even more preferably one or more compounds selected from the group consisting of compounds of the formulas (1) and (2), especially preferably a compound of the formula (1), especially preferably N-(hexadecyloxyhydroxypropyl)-N-hydroxyethylhexadecanamide.

<4> The emulsion composition according to any one of <1> to <3>, wherein the component (A) comprises one or more selected from the group consisting of ceramides, $C_{16}$-$C_{22}$ fatty acids, and $C_{16}$-$C_{22}$ higher alcohols, wherein a total content ratio of the ceramide, the $C_{16}$-$C_{22}$ fatty acid, and the $C_{16}$-$C_{22}$ higher alcohol to the component (A) is preferably from 20 to 100 mass %, more preferably from 30 to 100 mass %, further more preferably from 50 to 100 mass %, even more preferably from 75 to 100 mass %, especially preferably from 85 to 100 mass %, most preferably substantially 100 mass %, in the component (A).

<5> The emulsion composition according to any one of <1> to <4>, wherein the component (A) comprises a ceramide, wherein a content ratio of the ceramide to the component (A) is preferably from 20 to 100 mass %, more preferably from 30 to 100 mass %, further more preferably from 50 to 100 mass %, even more preferably from 75 to 100 mass %, especially preferably from 85 to 100 mass %, most preferably substantially 100 mass %, in the component (A).

<6> The emulsion composition according to any one of <1> to <5>, wherein the component (A) comprises one or more compounds selected from the group consisting of compounds of the formulas (1) and (2), wherein a content ratio of the one or more compounds selected from the group consisting of compounds of the formulas (1) and (2) to the component (A) is preferably from 20 to 100 mass %, more preferably from 30 to 100 mass %, further more preferably from 50 to 100 mass %, even more preferably from 75 to 100 mass %, especially preferably from 85 to 100 mass %, most preferably substantially 100 mass %, in the component (A).

<7> The emulsion composition according to any one of <1> to <6>, wherein the component (A) comprises N-(hexadecyloxyhydroxypropyl)-N-hydroxyethylhexadecanamide, wherein a content ratio of the N-(hexadecyloxyhydroxypropyl)-N-hydroxyethylhexadecanamide to the component (A) is preferably from 20 to 100 mass %, more preferably from 30 to 100 mass %, further more preferably from 50 to 100 mass %, even more preferably from 75 to 100 mass %, especially preferably from 85 to 100 mass %, most preferably substantially 100 mass %, in the component (A).

<8> The emulsion composition according to any one of <1> to <7>, wherein the component (A) comprises a ceramide, a $C_{16}$-$C_{22}$ fatty acid, and a $C_{16}$-$C_{22}$ higher alcohol, wherein a total content ratio of the $C_{16}$-$C_{22}$ fatty acid and the $C_{16}$-$C_{22}$ higher alcohol to a total amount of the ceramide, the $C_{16}$-$C_{22}$ fatty acid, and the $C_{16}$-$C_{22}$ higher alcohol in the component (A) is preferably 90 mass % or less, more preferably 70 mass % or less, further more preferably 50 mass % or less, even more preferably 25 mass % or less, especially preferably 10 mass % or less, most preferably substantially 0 mass %.

<9> The emulsion composition according to any one of <1> to <8>, wherein the component (A) comprises a ceramide and a $C_{16}$-$C_{22}$ fatty acid, wherein a total content ratio of the $C_{16}$-$C_{22}$ fatty acid to a total amount of the ceramide and the $C_{16}$-$C_{22}$ fatty acid in the component (A) is preferably 90 mass % or less, more preferably 70 mass % or less, further more preferably 50 mass % or less, even more preferably 25 mass % or less, especially preferably 10 mass % or less, most preferably substantially 0 mass %.

<10> The emulsion composition according to any one of <1> to <9>, wherein the component (A) comprises a ceramide and a $C_{16}$-$C_{22}$ higher alcohol, wherein a total content ratio of the $C_{16}$-$C_{22}$ higher alcohol to a total amount of the ceramide and the $C_1$-$C_{22}$ higher alcohol in the component (A) is preferably 90 mass % or less, more preferably 70 mass % or less, further more preferably 50 mass % or less, even more preferably 25 mass % or less, especially preferably 10 mass % or less, most preferably substantially 0 mass %.

<11> The emulsion composition according to any one of <1> to <10>, wherein the component (A) comprises N-(hexadecyloxyhydroxypropyl)-N-hydroxyethylhexadecanamide, a $C_{16}$-$C_{22}$ fatty acid, and a $C_{16}$-$C_{22}$ higher alcohol, wherein a total content ratio of the $C_{16}$-$C_{22}$ fatty acid and the $C_{16}$-$C_{22}$ higher alcohol to a total amount of the N-(hexadecyloxyhydroxypropyl)-N-hydroxyethylhexadecanamide), the $C_{16}$-$C_{22}$ fatty acid, and the $C_{16}$-$C_{22}$ higher alcohol in the component (A) is preferably 90 mass % or less, more preferably 70 mass % or less, further more preferably 50 mass % or less, even more preferably 25 mass % or less, especially preferably 10 mass % or less, most preferably substantially 0 mass %.

<12> The emulsion composition according to any one of <1> to <11>, wherein a content of the component (A) is preferably 2 mass % or more, more preferably 5 mass % or more, and preferably 15 mass % or less, more preferably 9 mass % or less, in the entire composition.

<13> The emulsion composition according to any one of <1> to <12>, wherein a content of the component (B) is preferably 1.5 mass % or more, more preferably 2 mass % or more, further more preferably 5 mass % or more, and preferably 20 mass % or less, more preferably 13 mass % or less, further more preferably 8.5 mass % or less, in the entire composition.

<14> The emulsion composition according to any one of <1> to <13>, wherein a molecular weight of the α-olefin oligomer as the component (C) is preferably 300 or more, more preferably 330 or more, further more preferably 360 or more, even more preferably 400 or more, and preferably 800 or less, more preferably 700 or less, further more preferably 600 or less, even more preferably 500 or less.

<15> The emulsion composition according to any one of <1> to <14>, wherein a viscosity at 25° C. of the α-olefin oligomer as the component (C) is preferably 5 mPa·s or more, more preferably 8 mPa·s or more, further more preferably 12 mPa·s or more, even more preferably 15 mPa·s or more, and preferably 50 mPa·s or less, more preferably 45 mPa·s or less, further more preferably 30 mPa·s or less, even more preferably 25 mPa·s or less.

<16> The emulsion composition according to any one of <1> to <15>, wherein an olefin moiety of the α-olefin oligomer as the component (C) is a hydrogenated polymer of linear aliphatic α-olefins having 4 to 12 carbon atoms, preferably linear aliphatic α-olefins having 6 to 12 carbon atoms, more preferably linear aliphatic α-olefins having 8 to 12 carbon atoms, further more preferably linear aliphatic α-olefins having 10 carbon atoms.

<17> The emulsion composition according to any one of <1> to <16>, wherein the α-olefin oligomer as the component (C) is a polymer of a linear aliphatic α-olefin having 4 to 12 carbon atoms, wherein a degree of polymerization is preferably from 3 to 6, more preferably from 3 to 4.

<18> The emulsion composition according to <17>, wherein a constituent ratio of components having the degree of polymerization of from 3 to 4 in the component (C) is preferably 50 mass % or more, more preferably 65 mass % or more, further more preferably 80 mass % or more, even more preferably substantially 100 mass %, in the component (C).

<19> The emulsion composition according to <17> or <18>, wherein a constituent ratio of components having the degree of polymerization of 5 or more in the component (C) is preferably less than 50 mass %, more preferably less than 35 mass %, further more preferably less than 20 mass %, even more preferably substantially zero, in the component (C).

<20> The emulsion composition according to any one of <1> to <19>, wherein a content of the component (C) is preferably 2 mass % or more, more preferably 4 mass % or more, and preferably 13 mass % or less, more preferably 8 mass % or less, in the entire composition.

<21> The emulsion composition according to any one of <1> to <20>, wherein a mass ratio of the component (A) to the component (B), (A)/(B), is preferably 0.1 or more, more preferably 0.38 or more, further more preferably 0.6 or more, even more preferably 1 or more, especially preferably 1.08 or more, and preferably 10 or less, more preferably 5 or less, further more preferably 3.3 or less, even more preferably 1.9 or less, especially preferably 1.4 or less.

<22> The emulsion composition according to any one of <1> to <21>, wherein a mass ratio of the component (A) to the component (C), (A)/(C), is preferably 0.1 or more, more preferably 0.4 or more, further more preferably 0.67 or more, even more preferably 1.1 or more, and preferably 10 or less, more preferably 5 or less, further more preferably 3.3 or less, even more preferably 2.1 or less.

<23> The emulsion composition according to any one of <1> to <22>, wherein a mass ratio of the component (B) to the component (C), (B)/(C), is preferably 0.1 or more, more preferably 0.48 or more, further more preferably 0.6 or more, even more preferably 0.8 or more, especially preferably 0.93 or more, and preferably 10 or less, more preferably 5 or less, further more preferably 3.3 or less, even more preferably 1.8 or less, especially preferably 1.47 or less.

<24> The emulsion composition according to any one of <1> to <23>, wherein the component (D) is preferably at least one selected from the group consisting of a silicone-based surfactant, polyoxyethylene hydrogenated castor oil, alkyl glyceryl ether, and sorbitan fatty acid ester, more preferably at least one selected from the group consisting of a silicone-based surfactant, polyoxyethylene hydrogenated castor oil, and alkyl glyceryl ether, further more preferably at least one selected from the group consisting of alkyl glyceryl ether and a silicone-based surfactant.

<25> The emulsion composition according to any one of <1> to <24>, wherein the component (D) is preferably a silicone-based surfactant, more preferably at least one selected from the group consisting of polyether-modified silicone, polyglycerin-modified silicone, polyether/alkyl co-modified silicone, and polyglycerin/alkyl co-modified silicone, further more preferably at least one selected from the group consisting of polyether-modified silicone and polyether/alkyl co-modified silicone, even more preferably polyether-modified silicone, even more preferably polyether-modified silicone having a linear backbone silicone chain, especially preferably at least one selected from the group consisting of PEG-3 dimethicone, PEG-10 dimethicone, and PEG-12 dimethicone, further more preferably at least one selected from the group consisting of PEG-3 dimethicone and PEG-12 dimethicone.

<26> The emulsion composition according to any one of <1> to <25>, wherein the component (D) preferably comprises alkyl glyceryl ether and a silicone-based surfactant at the same time, more preferably comprises isostearyl glyceryl ether and polyether-modified silicone, further more preferably comprises isostearyl glyceryl ether and one or more selected from the group consisting of PEG-3 dimethicone, PEG-10 dimethicone, and PEG-12 dimethicone, even more preferably comprises isostearyl glyceryl ether and one or more selected from the group consisting of PEG-3 dimethicone and PEG-12 dimethicone, and even more preferably comprises isostearyl glyceryl ether and PEG-3 dimethicone.

<27> The emulsion composition according to any one of <1> to <26>, wherein the nonionic surfactant as the component (D) has a HLB value of preferably from 1 to 7, more preferably from 1 to 6, further more preferably from 2 to 6, when the emulsion composition is a water-in-oil emulsion composition.

<28> The emulsion composition according to any one of <1> to <27>, wherein the component (D) preferably comprises a silicone-based surfactant having HLB of from 1 to 7.

<29> The emulsion composition according to any one of <1> to <26>, wherein the nonionic surfactant as the component (D) has a HLB value of preferably from 8 to 18, more preferably from 8 to 16, further more preferably from 8 to 14, when the emulsion composition is an oil-in-water emulsion composition.

<30> The emulsion composition according to any one of <1> to <29>, wherein a content of the nonionic surfactant as the component (D) is preferably 0.1 mass % or more, more preferably 0.5 mass % or more, further more preferably 1 mass % or more, even more preferably 1.5 mass % or more, and preferably 8 mass % or less, more preferably 5 mass % or less, further more preferably 3.5 mass % or less, even more preferably 3 mass % or less, in the entire composition.

<31> The emulsion composition according to any one of <1> to <30>, wherein a content of the water as the component (E) is preferably 10 mass % or more, more preferably 15 mass % or more, further more preferably 20 mass % or more, and preferably 85 mass % or less, more preferably 75 mass % or less, further more preferably 70 mass % or less, in the entire composition.

<32> The emulsion composition according to any one of <1> to <31>, preferably further comprising a polyhydric alcohol.

<33> The emulsion composition according to <32>, wherein the polyhydric alcohol preferably comprises one or more selected from the group consisting of at least a dihydric alcohol, a trihydric alcohol, a tetrahydric alcohol, and a sugar alcohol, more preferably comprises one or more selected from the group consisting of at least a dihydric alcohol, a trihydric alcohol, and a tetrahydric alcohol, further more preferably comprises one or more selected from the group consisting of at least propanediol, dipropylene glycol, 1,3-butylene glycol, glycerin, and diglycerin, even more preferably comprises one or more selected from the group consisting of at least dipropylene glycol, 1,3-butylene glycol, and glycerin, and especially preferably comprises at least glycerin.

<34> The emulsion composition according to <32> or <33>, wherein a content of the polyhydric alcohol is preferably 1 mass % or more, more preferably 5 mass % or more, further more preferably 10 mass % or more, and preferably 30 mass % or less, more preferably 20 mass % or less, further more preferably 15 mass % or less, in the entire composition.

<35> The emulsion composition according to any one of <1> to <34>, preferably further comprising an anionic surfactant.

<36> The emulsion composition according to <35>, wherein the anionic surfactant is preferably one or more selected from the group consisting of N-acylglutamic acid and a salt thereof, and N-acyl methyl taurine and a salt thereof, more preferably comprises one or more selected from the group consisting of N-stearoyl-L-glutamic acid and a salt thereof, and N-stearoyl-N-methyl taurine and a salt thereof, and further more preferably comprises one or more selected from the group consisting of sodium N-stearoyl-L-glutamate and sodium N-stearoyl-N-methyl taurine.

<37> The emulsion composition according to <35> or <36>, wherein a content of the anionic surfactant is preferably 0.1 mass % or more, more preferably 0.3 mass % or more, further more preferably 0.5 mass % or more, and preferably 5 mass % or less, more preferably 3 mass % or less, further more preferably 1 mass % or less, in the entire composition.

<38> The emulsion composition according to any one of <1> to <37>, wherein a content of an insoluble powder in the emulsion composition is preferably 30 mass % or less, more preferably 20 mass % or less, further more preferably 10 mass % or less, even more preferably 5 mass % or less, especially preferably substantially zero, in the entire composition.

<39> The emulsion composition according to any one of <1> to <38>, wherein a content of a UV protective agent other than a powder is preferably 20 mass % or less, more preferably 15 mass % or less, further more preferably 10 mass % or less, even more preferably 5 mass % or less, especially preferably substantially zero, in the entire composition.

<40> The emulsion composition according to any one of <1> to <39>, wherein the emulsion composition is preferably a water-in-oil emulsion composition.

<41> The emulsion composition according to any one of <1> to <39>, wherein the emulsion composition is preferably an oil-in-water emulsion composition.

<42> The emulsion composition according to any one of <1> to <41>, wherein the emulsion composition is preferably an emulsified cosmetic.

<43> The emulsion composition according to any one of <1> to <42>, wherein the emulsion composition is preferably in a dosage form of a cream, more preferably a skincare cream.

EXAMPLES

Examples 1 to 20 and Comparative Examples 1 to 4 Each water-in-oil emulsified cosmetic was produced according to the composition shown in Tables 1 to 3. The emulsified cosmetic was evaluated for its sleekness, easiness to spread, moist feeling of the skin after application, sustained moist feeling, heat sensation, and stability. The results are also shown in Tables 1 to 3.

The cosmetics of comparative Examples 1 and 3 could not be evaluated due to separation immediately after production and were thus described as "not evaluable". These cosmetics were also given "B" due to separation immediately after production in the evaluation of stability.

(Production Method)

The components (A) to (D) and other oil components were dissolved by heating at 85° C. to obtain an oil-phase mixture. The component (E) and other aqueous components were dissolved by heating at 85° C. to obtain an aqueous-phase mixture. The aqueous-phase mixture was added to the oil-phase mixture with stirring at 85° C. Then, the resulting mixture was cooled to 25° C. with stirring to obtain a water-in-oil emulsified cosmetic.

(Evaluation Method)

(1) Sleekness of Emulsified Cosmetic:

Four professional panelists evaluated each emulsified cosmetic filled in a transparent glass bottle (Wide-Mouth Standard Bottle No. 4, manufactured by AS ONE Corp.)

according to the criteria given below by visually observing the surface of the emulsified cosmetic from above the transparent glass bottle in a bright space. The results were indicated by a total score from the four professional panelists. An emulsified cosmetic having sleek appearance provides a luxury feeling.

4: Very sleek.
3: Sleek.
2: Not very sleek.
1: Not sleek.

(2) Easiness to Spread:

Four professional panelists evaluated easiness to spread upon application according to the criteria given below by washing their arms with a cleansing agent (Curel Face Wash, manufactured by Kao Corp.), and applying approximately 0.2 g of each emulsified cosmetic to the forearm at 25° C. The results were indicated by a total score from the four professional panelists.

The easiness to spread refers to smooth spreadability.

4: Very easy to spread.
3: Easy to spread.
2: Not very easy to spread.
1: Obviously difficult to spread.

(3) Moist Feeling of Skin after Application:

Four professional panelists evaluated fresh and moist feeling of the skin after application according to the criteria given below by washing their arms with a cleansing agent (Curel Face Wash, manufactured by Kao Corp.), and applying approximately 0.2 g of each emulsified cosmetic to the forearm at 25° C. The results were indicated by a total score from the four professional panelists.

The moist feeling of the skin is accompanied by fresh feeling.

4: The skin felt very moist.
3: The skin felt moist.
2: The skin did not feel very moist.
1: The skin did not feel moist.

(4) Sustained Moist Feeling:

Four professional panelists evaluated moist feeling of the skin after a lapse of 1 hour from application according to the criteria given below by washing their arms with a cleansing agent (Curel Face Wash, manufactured by Kao Corp.), and applying approximately 0.2 g of each emulsified cosmetic to the forearm at 25° C. The results were indicated by a total score from the four professional panelists.

4: The moist feeling did not change from immediately after application.
3: The moist feeling was slightly reduced from immediately after application.
2: The moist feeling was reduced from immediately after application.
1: The moist feeling was absent.

(5) Heat Sensation:

Four professional panelists evaluated heat sensation according to the criteria given below by washing their arms with a cleansing agent (Curel Face Wash, manufactured by Kao Corp.), applying approximately 0.2 g of each emulsified cosmetic to the forearm, entering a hot and humid (atmospheric temperature: 40° C., humidity: 75%) environment, and evaluating a degree of burdens on the skin due to heat sensation after acclimatization for 10 minutes. The results were indicated by a total score from the four professional panelists.

The heat sensation refers to a feeling as if heat stagnates on the skin exposed to a hot and humid condition at or above a certain level in the state of the skin given the emulsified cosmetic. When the heat sensation is reduced, the skin also feels less burdened.

4: The heat sensation as if sizzling heat stagnates was not perceived.
3: The heat sensation as if sizzling heat stagnates was very slightly perceived.
2: The heat sensation as if sizzling heat stagnates was perceived.
1: The heat sensation as if sizzling heat stagnates was strongly perceived.

(6) Stability (Appearance after Storage at 25° C. for 1 Day):

Each emulsified cosmetic was filled into a transparent glass bottle (Wide-Mouth Standard Bottle No. 4, manufactured by AS ONE Corp.) and stored at 25° C. for 1 day. Then, its appearance was visually evaluated from above and the side of the transparent glass bottle.

A: Not separated.
B: Separated.

(7) Stability (Appearance after Storage at 30° C. for 3 Days):

Each emulsified cosmetic was filled into a transparent glass bottle (Wide-Mouth Standard Bottle No. 4, manufactured by AS ONE Corp.) and stored at 30° C. for 3 days. Then, its appearance was visually evaluated from above and the side of the transparent glass bottle.

A: Not separated.
B: Separated.

(8) Stability (Appearance after Storage at 50° C. for 3 Days):

Each emulsified cosmetic was filled into a transparent glass bottle (Wide-Mouth Standard Bottle No. 4, manufactured by AS ONE Corp.) and stored at 50° C. for 3 days. Then, its appearance was visually evaluated from above and the side of the transparent glass bottle.

A: Not separated.
B: Separated.

TABLE 1

| | Component name (mass %) | Example 1 | Example 2 | Example 3 | Example 4 | Example 5 | Example 6 | Example 7 | Example 8 |
|---|---|---|---|---|---|---|---|---|---|
| | Allantoin *1 | | 0.5 | | | | | | |
| (A) | N-(Hexadecyloxyhydroxypropyl)-N-hydroxyethylhexadecanamide *2 | 8 | 8 | 3 | 8 | 8 | 8 | 8 | 1 |
| (D) | Isostearyl glyceryl *3 | 0.5 | 0.2 | 0.5 | 0.5 | 0.5 | 0.5 | 0.5 | 0.5 |
| | PEG-3 dimethicone *4 | 2 | 1.5 | 2 | 2 | 2 | 2 | 2 | 2 |
| | PEG-12 dimethicone *5 | | 0.2 | | | | | | |
| (C) | Hydrogenated polydecene *6 | 6 | 5.5 | 6 | 6 | 6 | 10 | 15 | 3 |
| (B) | Trisiloxane *7 | 7 | 7 | 7 | 3 | 10 | 7 | 7 | 3 |
| | Dimethicone (2CS) *8 | 4 | 4 | 4 | 4 | 4 | 4 | 4 | 4 |
| | Dimethicone (6CS) *9 | 2 | 2 | 2 | 2 | 2 | 2 | 2 | 2 |
| | Mg sulfate *10 | | 0.3 | | | | | | |
| | Glycerin (86%) *11 | 15 | 15 | 15 | 15 | 15 | 15 | 15 | 15 |
| | Eucalyptus globulus leaf extract *12 | | 0.33 | | | | | | |

TABLE 1-continued

| | | | | | | | | | |
|---|---|---|---|---|---|---|---|---|---|
| | Methylparaben *13 | 0.2 | 0.2 | 0.2 | 0.2 | 0.2 | 0.2 | 0.2 | 0.2 |
| | Succinic acid *14 | | 0.1 | | | | | | |
| | Na hydroxide (48%) *15 | | 0.07 | | | | | | |
| (E) | Purified water | balance | balance | balance | balance | balance | balance | balance | balance |
| | Total | 100 | 100 | 100 | 100 | 100 | 100 | 100 | 100 |
| | Total amount of (A) | 8 | 8 | 3 | 8 | 8 | 8 | 8 | 1 |
| | Total amount of (B) | 7 | 7 | 7 | 3 | 10 | 7 | 7 | 3 |
| | Total amount of (C) | 6 | 5.5 | 6 | 6 | 6 | 10 | 15 | 3 |
| | Total amount of (D) | 2.5 | 1.9 | 2.5 | 2.5 | 2.5 | 2.5 | 2.5 | 2.5 |
| | (A)/(B) | 1.14 | 1.14 | 0.43 | 2.67 | 0.8 | 1.14 | 1.14 | 0.33 |
| | (A)/(C) | 1.33 | 1.45 | 0.5 | 1.33 | 1.33 | 0.8 | 0.53 | 0.33 |
| | (B)/(C) | 1.17 | 1.27 | 1.17 | 0.5 | 1.67 | 0.7 | 0.47 | 1 |
| | Sleekness of emulsified cosmetic | 16 | 16 | 16 | 8 | 16 | 16 | 14 | 16 |
| | Easiness to spread | 16 | 16 | 15 | 9 | 16 | 15 | 10 | 14 |
| | Moist feeling of skin after application | 16 | 16 | 14 | 12 | 14 | 14 | 9 | 11 |
| | Sustained moist feeling | 16 | 16 | 11 | 14 | 14 | 15 | 13 | 10 |
| | Heat sensation | 16 | 16 | 15 | 10 | 16 | 15 | 9 | 12 |
| | Stability (appearance after storage at 25° C. for 1 day) | A | A | A | A | A | A | A | A |
| | Stability (appearance after storage at 30° C. for 3 days) | A | A | A | A | A | A | A | A |
| | Stability (appearance after storage at 50° C. for 3 days) | A | A | A | A | A | A | A | A |

| | Component name (mass %) | Example 9 | Example 10 | Example 11 | Example 12 | Comparative Example 1 | Comparative Example 2 | Comparative Example 3 |
|---|---|---|---|---|---|---|---|---|
| | Allantoin *1 | | | | | | | |
| (A) | N-(Hexadecyloxyhydroxypropyl)-N-hydroxyethylhexadecanamide *2 | 8 | 12 | 8 | 8 | 8 | 8 | |
| (D) | Isostearyl glyceryl *3 | 0.5 | 0.5 | 0.5 | 0.5 | 0.5 | 0.5 | 0.5 |
| | PEG-3 dimethicone *4 | 2 | 2 | 2 | 2 | 2 | 2 | 2 |
| | PEG-12 dimethicone *5 | | | | | | | |
| (C) | Hydrogenated polydecene *6 | 3 | 3 | 3 | 6 | 6 | 6 | 6 |
| (B) | Trisiloxane *7 | 3 | 3 | 15 | 7 | | | 7 |
| | Dimethicone (2CS) *8 | 4 | 4 | 4 | 4 | 4 | 11 | 4 |
| | Dimethicone (6CS) *9 | 2 | 2 | 2 | 2 | 2 | 2 | 2 |
| | Mg sulfate *10 | | | | | | | |
| | Glycerin (86%) *11 | 15 | 15 | 15 | | 15 | 15 | 15 |
| | Eucalyptus globulus leaf extract *12 | | | | | | | |
| | Methylparaben *13 | 0.2 | 0.2 | 0.2 | 0.2 | 0.2 | 0.2 | 0.2 |
| | Succinic acid *14 | | | | | | | |
| | Na hydroxide (48%) *15 | | | | | | | |
| (E) | Purified water | balance | balance | balance | balance | balance | balance | balance |
| | Total | 100 | 100 | 100 | 100 | 100 | 100 | 100 |
| | Total amount of (A) | 8 | 12 | 8 | 8 | 8 | 8 | 0 |
| | Total amount of (B) | 3 | 3 | 15 | 7 | 0 | 0 | 7 |
| | Total amount of (C) | 3 | 3 | 3 | 6 | 6 | 6 | 6 |
| | Total amount of (D) | 2.5 | 2.5 | 2.5 | 2.5 | 2.5 | 2.5 | 2.5 |
| | (A)/(B) | 2.67 | 4 | 0.53 | 1.14 | — | — | — |
| | (A)/(C) | 2.67 | 4 | 2.67 | 1.33 | 1.33 | 1.33 | — |
| | (B)/(C) | 1 | 1 | 5 | 1.17 | — | — | 1.17 |
| | Sleekness of emulsified cosmetic | 12 | 9 | 8 | 16 | Not evaluable | 8 | Not evaluable |
| | Easiness to spread | 11 | 8 | 15 | 16 | Not evaluable | 6 | Not evaluable |
| | Moist feeling of skin after application | 12 | 10 | 10 | 14 | Not evaluable | 11 | Not evaluable |
| | Sustained moist feeling | 13 | 10 | 9 | 15 | Not evaluable | 12 | Not evaluable |
| | Heat sensation | 11 | 9 | 13 | 16 | Not evaluable | 7 | Not evaluable |
| | Stability (appearance after storage at 25° C. for 1 day) | A | A | A | A | B | A | B |
| | Stability (appearance after storage at 30° C. for 3 days) | A | A | A | A | B | A | B |
| | Stability (appearance after storage at 50° C. for 3 days) | A | A | A | A | B | A | B |

TABLE 2

| | Component name (mass %) | Example 13 | Example 14 | Example 15 | Example 16 | Example 17 | Example 18 | Comparative Example 4 |
|---|---|---|---|---|---|---|---|---|
| (A) | N-(Hexadecyloxyhydroxypropyl)-N-hydroxyethylhexadecanamide *2 | | | 3 | 8 | 3 | 3 | 3 |
| | Stearyl alcohol *16 | 3 | | | | | | 0.5 |
| | Ceramide NG *17 | | 3 | | | | | |

TABLE 2-continued

| | Component name (mass %) | Example 13 | Example 14 | Example 15 | Example 16 | Example 17 | Example 18 | Comparative Example 4 |
|---|---|---|---|---|---|---|---|---|
| (D) | Isostearyl glyceryl *3 | 0.5 | 2 | 0.5 | 0.5 | 2 | | |
| | PEG-3 dimethicone *4 | 2 | 2 | 2 | | | 4 | |
| | PEG-10 hydrogenated castor oil *18 | | | | 2 | | | 2 |
| (C) | Hydrogenated polydecene *6 | 6 | 6 | | 6 | 6 | 6 | |
| | Hydrogenated polydecene *19 | | | 6 | | | | |
| (B) | Trisiloxane *7 | 7 | 7 | 7 | 7 | 7 | 7 | 7 |
| | Hydrogenated polyisobutene *20 | | | | | | | 6 |
| | Dimethicone (2CS) *8 | 4 | 4 | 4 | | | 4 | 4 |
| | Dimethicone (6CS) *9 | 2 | 2 | 2 | | | 2 | 2 |
| | Glycerin (86%) *11 | 15 | 15 | 15 | 15 | 15 | 15 | 15 |
| | Methylparaben *13 | 0.2 | 0.2 | 0.2 | 0.2 | 0.2 | 0.2 | 0.2 |
| (E) | Purified water | balance | balance | balance | balance | balance | balance | balance |
| | Total | 100 | 100 | 100 | 100 | 100 | 100 | 100 |
| | Total amount of (A) | 3 | 3 | 3 | 8 | 3 | 3 | 3.5 |
| | Total amount of (B) | 7 | 7 | 7 | 7 | 7 | 7 | 7 |
| | Total amount of (C) | 6 | 6 | 6 | 6 | 6 | 6 | 0 |
| | Total amount of (D) | 2.5 | 4 | 2.5 | 2.5 | 2 | 4 | 2 |
| | (A)/(B) | 0.43 | 0.43 | 0.43 | 1.14 | 0.43 | 0.43 | 0.5 |
| | (A)/(C) | 0.5 | 0.5 | 0.5 | 1.33 | 0.5 | 0.5 | — |
| | (B)/(C) | 1.17 | 1.17 | 1.17 | 1.17 | 1.17 | 1.17 | — |
| | Sleekness of emulsified cosmetic | 16 | 14 | 15 | 16 | 14 | 15 | 5 |
| | Easiness to spread | 12 | 12 | 15 | 9 | 12 | 13 | 7 |
| | Moist feeling of skin after application | 13 | 11 | 11 | 10 | 10 | 12 | 7 |
| | Sustained moist feeling | 8 | 15 | 10 | 15 | 14 | 14 | 8 |
| | Heat sensation | 11 | 13 | 14 | 9 | 11 | 11 | 6 |
| | Stability (appearance after storage at 25° C. for 1 day) | A | A | A | A | A | A | A |
| | Stability (appearance after storage at 30° C. for 3 days) | A | A | A | A | A | A | A |
| | Stability (appearance after storage at 50° C. for 3 days) | B | A | A | A | A | A | A |

TABLE 3

| | Component name (mass %) | Example 19 | Example 20 |
|---|---|---|---|
| (A) | N-(Hexadecyloxyhydroxypropyl)-N-hydroxyethylhexadecanamide *2 | 12 | 8 |
| (D) | Isostearyl glyceryl *3 | 0.5 | 0.5 |
| | PEG-3 dimethicone *4 | 2 | 2 |
| (C) | Hydrogenated polydecene *6 | 6 | 3 |
| (B) | Trisiloxane *7 | 7 | 7 |
| | Dimethicone (2CS) *8 | 4 | 4 |
| | Dimethicone (6CS) *9 | 2 | 2 |
| | Glycerin (86%) *11 | 15 | 15 |
| | Methylparaben *13 | 0.2 | 0.2 |
| (E) | Purified water | balance | balance |
| | Total | 100 | 100 |
| | Total amount of (A) | 12 | 8 |
| | Total amount of (B) | 7 | 7 |
| | Total amount of (C) | 6 | 3 |
| | Total amount of (D) | 2.5 | 2.5 |
| | (A)/(B) | 1.71 | 1.14 |
| | (A)/(C) | 2 | 2.67 |
| | (B)/(C) | 1.17 | 2.33 |
| | Sleekness of emulsified cosmetic | 10 | 11 |
| | Easiness to spread | 11 | 15 |
| | Moist feeling of skin after application | 12 | 10 |
| | Sustained moist feeling | 12 | 12 |
| | Heat sensation | 13 | 15 |

TABLE 3-continued

| Component name (mass %) | Example 19 | Example 20 |
|---|---|---|
| Stability (appearance after storage at 25° C. for 1 day) | A | A |
| Stability (appearance after storage at 30° C. for 3 days) | A | A |
| Stability (appearance after storage at 50° C. for 3 days) | A | A |

*1: allantoin (INCI name: Allantoin): manufactured by Kawaken Fine Chemicals Co., Ltd., S-allantoin,

*2: N-(hexadecyloxyhydroxypropyl)-N-hydroxyethylhexadecanamide (INCI name: Cetyl-PG Hydroxyethyl Palmitamide): manufactured by Kao Corp., SOFCARECERAMIDE SL-E,

*3: isostearyl glyceryl (INCI name: Isostearyl Glyceryl Ether): manufactured by Kao Corp., PENETOL GE-IS,

*4: PEG-3 dimethicone (INCI name: PEG-3 Dimethicone): manufactured by Shin-Etsu Chemical Co., Ltd., silicone KF-6015 (-G),

*5: PEG-12 dimethicone (INCI name: PEG-12 Dimethicone): Dow Silicone Corporation, DOWSIL SH 3775 M FLUID(-G),

*6: hydrogenated polydecene (INCI name: Hydrogenated Polydecene): Vantage Specialty Chemicals, SILKFLO 364,

*7: trisiloxane (INCI name: Trisiloxane): manufactured by Shin-Etsu Chemical Co., Ltd., Silicone KF-96A-1CS(-G),

*8: dimethicone (2CS) (INCI name: Dimethicone): manufactured by Shin-Etsu Chemical Co., Ltd., Silicone KF-96L-2CS(-G),

*9: dimethicone (6CS) (INCI name: Dimethicone): manufactured by Shin-Etsu Chemical Co., Ltd., Silicone KF-96A-6CS(-G),

*10: Mg sulfate (INCI name: Magnesium Sulfate): manufactured by Umai Chemical., Ltd., Umai Reagent First Grade Magnesium sulfate,

*11: glycerin (86%) (INCI name: Glycerin): manufactured by Kao Corp., 86% Glycerin V (mixture of 86% glycerin and 14% water),

*12: *Eucalyptus globulus* leaf extract (INCI name: *Eucalyptus Globulus* Leaf Extract): manufactured by Tochimoto Tenkaido Co., Ltd., *Eucalyptus Globulus* Liquid Extract EBL,

*13: methylparaben (INCI name: Methylparaben): manufactured by Ueno Fine Chemicals Industry, Ltd., MEKKINS-M (methyl p-hydroxybenzoate),

*14: succinic acid (INCI name: Succinic Acid): manufactured by Nippon Shokubai Co., Ltd., Succinic acid,

*15: Na hydroxide (48%) (INCI name: Sodium Hydroxide): manufactured by Nankai Chemical Co., Ltd., 48% Caustic Soda (food additive) (Q),

*16: stearyl alcohol (INCI name: Stearyl Alcohol): manufactured by Kao Corp., KALCOL 8098,

*17: ceramide NG (INCI name: Ceramide NG): manufactured by Croda Japan K.K., Ceramide 2,

*18: PEG-10 hydrogenated castor oil (INCI name: PEG-10 Hydrogenated Castor Oil): manufactured by Nippon Surfactant Industries Co., Ltd., NIKKOL HCO-10,

*19: hydrogenated polydecene (INCI name: Hydrogenated Polydecene): Vantage Specialty Chemicals, SILKFLO 366,

*20: hydrogenated polyisobutene (INCI name: Hydrogenated Polyisobutene): manufactured by NOF Corp., PARLEAM EX

The invention claimed is:

1. An emulsion composition comprising the following components (A), (B), (C), (D), and (E):

(A) 0.1 to 20 mass % of an oil component having a melting point of from 50 to 150° C.;

(B) 1 to 30 mass % of octamethyltrisiloxane;

(C) 1 to 13 mass % of an α-olefin oligomer;

(D) a nonionic surfactant; and (E) water, wherein a mass ratio of the component (A) to the component (B), (A)/(B), is from 0.1 to 3.3, and the component (D) is one or more selected from the group consisting of an alkyl glyceryl ether and a silicone-based surfactant, and the content of the component (D) is 1 mass % or more.

2. The emulsion composition according to claim 1, wherein a mass ratio of the component (A) to the component (C), (A)/(C), is from 0.1 to 10.

3. The emulsion composition according to claim 1, wherein a mass ratio of the component (A) to the component (B), (A)/(B), is from 1 to 1.9.

4. The emulsion composition according to claim 1, wherein the component (D) comprises a silicone-based surfactant having a hydrophilic-lipophilic balance (HLB) of from 1 to 7.

5. The emulsion composition according to claim 1, wherein the component (A) comprises one or more selected from the group consisting of ceramides and $C_{16}$-$C_{22}$ higher alcohols.

6. The emulsion composition according to claim 1, wherein the component (A) comprises a ceramide.

7. The emulsion composition according to claim 1, wherein the component (A) comprises N-(hexadecyloxyhydroxypropyl)-N-hydroxyethylhexadecanamide.

8. The emulsion composition according to claim 1, wherein the emulsion composition is a water-in-oil emulsion composition.

9. The emulsion composition according to claim 1, which comprises 2 mass % to 9 mass % of said component (A).

10. The emulsion composition according to claim 1, which comprises 5 mass % to 9 mass % of said component (A).

11. The emulsion composition according to claim 1, which comprises 2 mass % to 13 mass % of component (C).

12. The emulsion composition according to claim 1, which comprises 4 mass % to 8 mass % of component (C).

13. The emulsion composition according to claim 1, which comprises 1 mass % to 8 mass % of component (D).

14. The emulsion composition according to claim 1, which comprises 1 mass % to 5 mass % of component (D).

15. The emulsion composition according to claim 1, which comprises to 1 mass % to 3.5 mass % of component (D).

16. The emulsion composition according to claim 1, which comprises as component (D) an alkyl glyceryl ether which is selected from the group consisting of 2-ethylhexyl glyceryl ether, isododecyl glyceryl ether, isostearyl glyceryl ether, and mixtures thereof.

17. The emulsion composition according to claim 1, which comprises as component (D) a polyether-modified silicone selected from the group consisting of PEG-3 dimethicone, PEG-10 dimethicone, PEG-12 dimethicone, and mixtures thereof.

18. The emulsion composition according to claim 1, wherein a mass ratio of the component (A) to the component (C), (A)/(C), is from 0.67 to 3.3.

19. The emulsion composition according to claim 1, wherein a mass ratio of the component (A) to the component (B), (A)/(B), is from 0.6 to 3.3.

20. An emulsion composition comprising the following components (A), (B), (C), (D), and (E):

(A) 0.1 to 20 mass % of an oil component having a melting point of from 50 to 150° C.;

(B) 1 to 30 mass % of octamethyltrisiloxane;

(C) 1 to 13 mass % of an α-olefin oligomer;

(D) a nonionic surfactant; and (E) water, wherein a mass ratio of the component (A) to the component (B), (A)/(B), is from 0.1 to 3.3, and wherein the component (D) has a HLB value of 1 to 6, and wherein, when the component (D) is constituted by two or more surfactants, both of their HLB values are from 1 to 6.

* * * * *